(12) United States Patent
Huang

(10) Patent No.: US 8,895,751 B2
(45) Date of Patent: *Nov. 25, 2014

(54) PROCESS OF MANUFACTURING BENZOBISTHIAZOLE BUILDING BLOCKS FOR CONJUGATED POLYMERS

(71) Applicant: Phillips 66 Company, Houston, TX (US)

(72) Inventor: Hui Huang, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/954,229

(22) Filed: Jul. 30, 2013

(65) Prior Publication Data

US 2014/0058111 A1 Feb. 27, 2014

Related U.S. Application Data

(60) Provisional application No. 61/692,405, filed on Aug. 23, 2012.

(51) Int. Cl.
C07D 513/04 (2006.01)
C07D 277/68 (2006.01)

(52) U.S. Cl.
CPC ............ *C07D 513/04* (2013.01); *C07D 277/68* (2013.01)
USPC ....................................................... 548/151

(58) Field of Classification Search
None
See application file for complete search history.

(56) References Cited

U.S. PATENT DOCUMENTS

| 8,703,960 B2 * | 4/2014 | Huang ........................... 548/151 |
| 2010/0078074 A1 | 4/2010 | Yang et al. |

FOREIGN PATENT DOCUMENTS

| EP | 0611754 | 8/1994 |
| WO | 2011028827 | 3/2011 |

OTHER PUBLICATIONS

Mrs. A. Chatterjee & Biswanath Das, N. Adityachaudhury & Mrs. S. Deb Kirtaniya, Studies on Aryl-& Diaryl-thioureas & Their Insecticidal Activity, 1979, pp. 163-164.

Bei-Sih Liao and Shiuh-Tzung Liu, "Diamination of Phenylene Dihalides Catalyzed by a Dicopper Complex", The Journal of Organic Chemistry, 2012, American Chemical Society, pp. 6653-6656.

Min Wang, Mingzhang Gao, Bruce H. Mock, Kathy D. Miller, George W. Sledge, Gary D. Hutchins and Qi-Huang Zheng, "Synthesis of Carbon-11 Labeled Fluorinated 2-Arylbenzothiazoles as Novel Potential PET Cancer Imaging Agents", ScienceDirect, Bioorganic Medicinal Chemistry 14 (2006), pp. 8599-8607.

Shashikant V. Bhandari, Kailash G. Bothara, Ajit A. Patil, Trupti S. Chitre, Aniket P. Sarkate, Suraj T. Gore, Sudarshan C. Dangre, Chetan V. Khachane, "Design, Synthesis and Pharmacological Screening of Novel Antihypertensive Agents Using Hybrid Approach", Biooraganic & Medicinal Chemistry 17 (2009), pp. 390-400.

Chunjian Liu, James Lin, Sidney Pitt, Rosemary F. Zhang, John S. Sack, Susan E. Kiefer, Kevin Kish, Arthur M. Dowsyko, Hongjian Zhang, Punit H. Marathe, James Trzaskos, Murray Mckinnon, John H. Dodd, Joel C. Barrish, Gary L Schieven and Katerina Leftheris, "Benzothiazole Based Inhibitors of p638α MAP Kinase", ScienceDirect, Bioorganic & Medicinal Chemistry Letters 18 (2008), pp. 1874-1879.

Justus K. Landquist, "Diaminobenzobisthiazoles and Related Compounds", J. Chem. Soc. (C), 1967, XP009023069, pp. 2212-2220.

PCT Notification of Transmittal of the International Search Report and the Written Opinion of the International Searching Authority, or the Declaration, International Application No. PCT/US2013/052719; International Filing Date: Sep. 16, 2013, 14 pages.

Achala Bhrwalka, Jared F. Mike, Meng He, Jeremy J. Intemann, Toby Nelson, Monique D. Ewan, Robert A. Roggers, Zhiqun Lin, and Malaika Jeffries-El, "Quarterthiophene—Benzobisazole Copolymers for Photovoltaic Cells: Effect of Heteroatom Placement and Substitution on the Optical and Electronic Properties", Macromolecules Article, ACS Publications, 2011, American Chemical Society, pp. 9611-9617.

Louis S. Hegedus, Roy R. Odle, Peter M. Winton, and Paul R. Weider, "Synthesis of 2,5-Disubstituted 3,6-Diamino-1,4-benzoquinones", XP-008136244, 1982 American Chemical Society, vol. 47, pp. 2607-2613.

Hualong Pan, Yuning Li, Yilang Wu, Ping Liu, Beng S. Ong, Shiping Zhu, Gu Xu, "Low-Temperature, Solution-Processed, High-Mobility Polymer Semiconductors for Thin-Film Transistors", XP-009136480, J. Am. Chem. Soc. 2007, vol. 129, pp. 4112-4113.

Yongye Liang, Danqin Feng, Yue Wu, Szu-Ting Tsai, Gang Li, Claire Ray, and Luping Yu, "Highly Efficient Solar Cell Polymers Developed via Fine-Tuning of Structural and Electronic Properties, JACS Articles," XP-002639687, J. Am. Chem. Soc. 2009, vol. 131, pp. 7792-7799.

\* cited by examiner

*Primary Examiner* — Michael Barker
(74) *Attorney, Agent, or Firm* — Phillips 66 Company

(57) ABSTRACT

A process comprising the step of synthesizing 2,6-dibromo-4,8-dihexylbenzo[1,2-d:4,5-d']bis(thiazole) from 2,5-dihyxylbenzene-1,4-diamine.

9 Claims, 20 Drawing Sheets

_US 8,895,751 B2_

PROCESS OF MANUFACTURING BENZOBISTHIAZOLE BUILDING BLOCKS FOR CONJUGATED POLYMERS

CROSS-REFERENCE TO RELATED APPLICATIONS

This application is a Non-Provisional application which claims the benefit of and priority to U.S. Provisional Application Ser. No. 61/692,405 filed Aug. 23, 2012, entitled "Process of Manufacturing Benzobisthiazole Building Blocks for Conjugated Polymers," which is hereby incorporated by reference.

STATEMENT REGARDING FEDERALLY SPONSORED RESEARCH OR DEVELOPMENT

None.

FIELD OF THE INVENTION

Process for manufacturing a weak donor moiety which can be used in the synthesis of novel push-pull conjugated copolymers.

BACKGROUND OF THE INVENTION

A solar cell is an electrical device that converts the energy of light directly into electricity by the photovoltaic effect. It is a form of photoelectric cell (in that its electrical characteristics—e.g. current, voltage, or resistance—vary when light is incident upon it) which, when exposed to light, can generate and support an electric current without being attached to any external voltage source.

The efficiency of a solar cell may be broken down into reflectance efficiency, thermodynamic efficiency, charge carrier separation efficiency and conductive efficiency. The overall efficiency is the product of each of these individual efficiencies.

Bulk-heterojunction polymer solar cells have emerged as an attractive type of cost-effective solar energy electrical power transforming device. Recently, great progress in the development of new photo-harvesting materials and device optimizations have been achieved in this field, resulting in the significant improvement of the power conversion efficiencies of polymer solar cells from around 1% to higher than 8.0%. The rational design and fine tailoring of the molecular structures of donor polymers significantly contributed to these prominent advances. Among all kinds of donor polymers, push-pull conjugated polymers, which consist of alternating electron-rich and electron-deficient units have been most extensively developed and have dominated the library of donor materials for polymer solar cells, because their intrinsic optical and electronic properties can be readily tuned to the desired situation by controlling the intramolecular charge transfer from donor unit to acceptor unit.

Ideal conjugated polymers as donors for solar cells should have a narrow band gap for a broad light absorption, a deep highest occupied molecular orbital for a high open-circuit voltage, and a high charge mobility for a low series resistance. A push pull strategy to achieve these types of conjugated polymers is to combine a weak electron-rich moiety with a strong electron-deficient moiety.

BRIEF SUMMARY OF THE DISCLOSURE

A process comprising the step of synthesizing 2,6-dibromo-4,8-dihexylbenzo[1,2-d:4,5-d']bis(thiazole) from 2,5-dihyxylbenzene-1,4-diamine.

In one embodiment the process involves the steps of:
(a) synthesizing 2,5-dihyxylbenzene-1,4-diamine from 1,4-dibromohexyl benzene;
(b) synthesizing 1,1'-(2,5-dihexyl-1,4-phenylene)bis(thiourea) from 2,5-dihyxylbenzene-1,4-diamine;
(c) synthesizing 4,8-dihexylbenzo[1,2-d:4,5-d']bis(thiazole)-2,6-diamine from 1,1'-(2,5-dihexyl-1,4-phenylene)bis(thiourea); and
(d) synthesizing 2,6-dibromo-4,8-dihexylbenzo[1,2-d:4,5-d']bis(thiazole) from 4,8-dihexylbenzo[1,2-d:4,5-d']bis(thiazole)-2,6-diamine.

In yet another embodiment the process involves the steps of:
(a) synthesizing 2,5-dihyxylbenzene-1,4-diamine from 1,4-dibromohexyl benzene;
(b) synthesizing N,N'-(((2,5-dihexyl-1,4-phenylene)bis(azanediyl))bis(carbonothioyl))dibenzamine from 2,5-dihyxylbenzene-1,4-diamine;
(c) synthesizing 1,1'-(2,5-dihexyl-1,4-phenylene)bis(thiourea) from N,N'-(((2,5-dihexyl-1,4-phenylene)bis(azanediyl))bis(carbonothioyl))dibenzamide;
(d) synthesizing 4,2-dihexylbenzo[1,2-d:4,5-d']bis(thiazole)-2,6-diamine from 1,1'-(2,5-dihexyl-1,4-phenylene)bis(thiourea); and
(e) synthesizing 2,6-dibromo-4,8-dihexylbenzo[1,2-d:4,5-d']bis(thiazole) from 4,8-dihexylbenzo[1,2-d:4,5-d']bis(thiazole)-2,6-diamine.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Figure 1A:
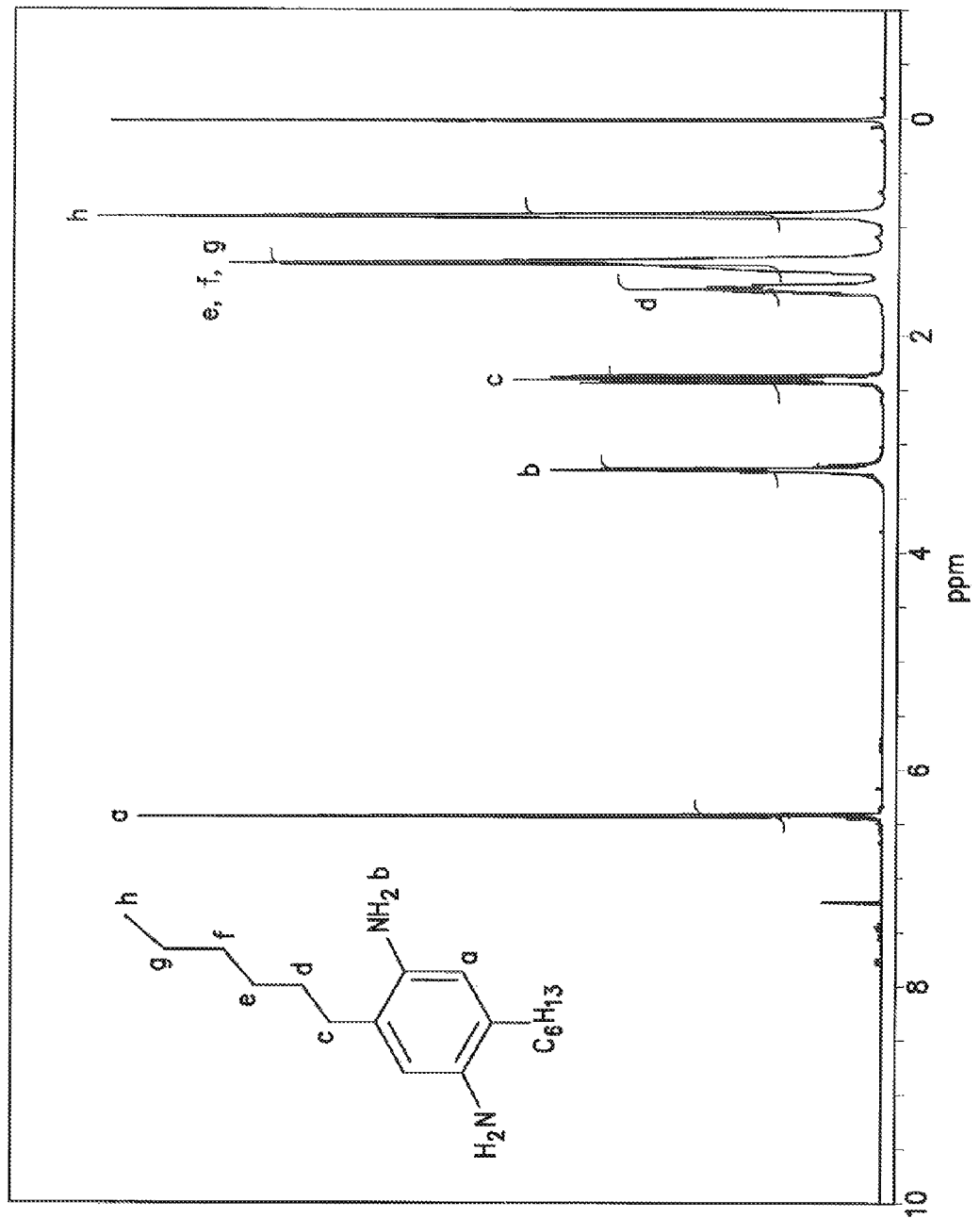
FIG. 1*a* depicts a $^1$H NMR spectrum of 2,5-dihyxylbenzene-1,4-diamine in CDCl$_3$.

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

The current disclosure depicts a process of synthesizing 2,6-dibromo-4,8-dihexylebenzo[1,2-d:4,5-d']bis(thiazole) from 2,5-dihyxylbenzene-1,4-diamine.

In one embodiment 2,5-dihyxylbenzene-1,4-diamine is synthesized from 1,4-dibromohexyl benzene prior to synthesizing 2,6-dibromo-4,8-dihexylbenzo[1,2-d:4,5-d']bis(thiazole).

In another embodiment 1,1'-(2,5-dihexyl-1,4-phenylene)bis(thioruea) is synthesized from 2,5-dihyxylbenzene-1,4-diamine prior to synthesizing 2,6-dibromo-4,8-dihexylbenzo[1,2-d:4,5-d']bis(thiazole).

In yet another embodiment 4,8-dihexylbenzo[1,2-d:4,5-d']bis(thiazole)-2,6-diamine is synthesized from 1,1'-(2,5-dihexyl-1,4-phenylene)bis(thiourea) prior to synthesizing 2,6-dibromo-4,8-dihexylbenzo[1,2-d:4,5-d']bis(thiazole).

It is also possible in one embodiment that N,N'-(((2,5-dihexyl-1,4-phenylene)bis(azanediyl))bis(carbonothioyl) dibenzamide is synthesized from 2,5-dihyxylbenzene-1,4-diamine prior to synthesizing 2,6-dibromo-4,8-dihexylbenzo[1,2-d:4, 5-d']bis(thiazole).

Additionally, in one embodiment 1,1'-(2,5-dihexyl-1,4-phenylene)bis(thiourea) is synthesized from N,N'-(((2,5-dihexyl-1,4-phenylene)bis(azanediyl)bis(carbonothioyl)) dibenzamide prior to synthesizing 2,6-dibromo-4,8-dihexylbenzo[1,2-d:4,5d']bis(thiazole).

The result of this process can create the following structure:

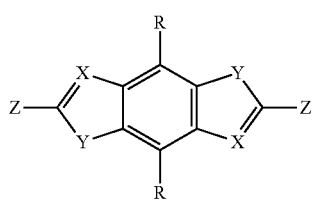

In one embodiment Z can be any known halogen. Halogen elements are currently known to be a series of nonmetal elements from group 17 of the periodic table. These elements include fluorine, chlorine, bromine, iodine and astatine.

In one embodiment X can be any nonmetal element such as nitrogen, oxygen, phosphorus, sulfur, or selenium.

In another embodiment Y can be any nonmetal element such as nitrogen, oxygen, phosphorus, sulfur, or selenium.

Although not required, in one embodiment X and Y are different elements.

In one embodiment R is a n-alkane chain. The n-alkane chain can be 3, 4, 5, 6, 7, 8, 9, or even 10 carbon chains long. In other embodiments the n-alkane chain can be greater than 10, 15, 20 even 35 carbon chains long.

2,6-dibromo-4,8-dihexylbenzo[1,2-d:4,5-d']bis(thiazole) can also be structurally depicted as:

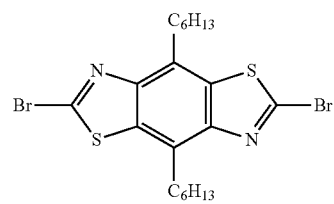

The following examples of certain embodiments of the invention are given. Each example is provided by way of explanation of the invention, one of many embodiments of the invention, and the following examples should nut be read to limit, or define, the scope of the invention.

Example 1

Preparation of 2,5-dihyxylbenzene-1,4-diamine from 1,4-dibromohexyl benzene

A toluene-(400 mL) solution of benzophenoeimine (18.1 g, 100 mmol), 1, 4-dibromo-hexyl benzene (20 g, 50 mmol), t-BuONa (10 g), and (DPPF)₂PdCl₂ (2 g) was refluxed under argon. The mixture was refluxed for 72 hours and then cooled to room temperature. Water (70 mL) and aqeous HCl (37%, 70 mL) were added to the mixture, which was then refluxed for 10 hours and cooled to room temperature. The solvent was removed by rotary evaporator. The solid was stirred with ethyl ether (300 mL) for 2 days, then filtered, washed with a small amount of ether, and dried, which was stirred in ether (200 mL) with aqueous NaOH (5 M, 300 mL). The ether phase was separated and dried over MgSO₄ and run through a short, silica gel column (6 cm×6 cm). The solvent was removed to leave a dark brown solid, which was dissolved in ethanol (50 mL). After sitting overnight, 2,5-dihyxylbenzene-1,4-diamine needles had formed in the solution. The needles were collected through filtration (yield: 6 g, 43%).

FIG. 1a depicts a ¹H NMR spectrum of 2,5-dihyxylbenzene-1,4-diamine in CDCl₃.

Figure 1B:
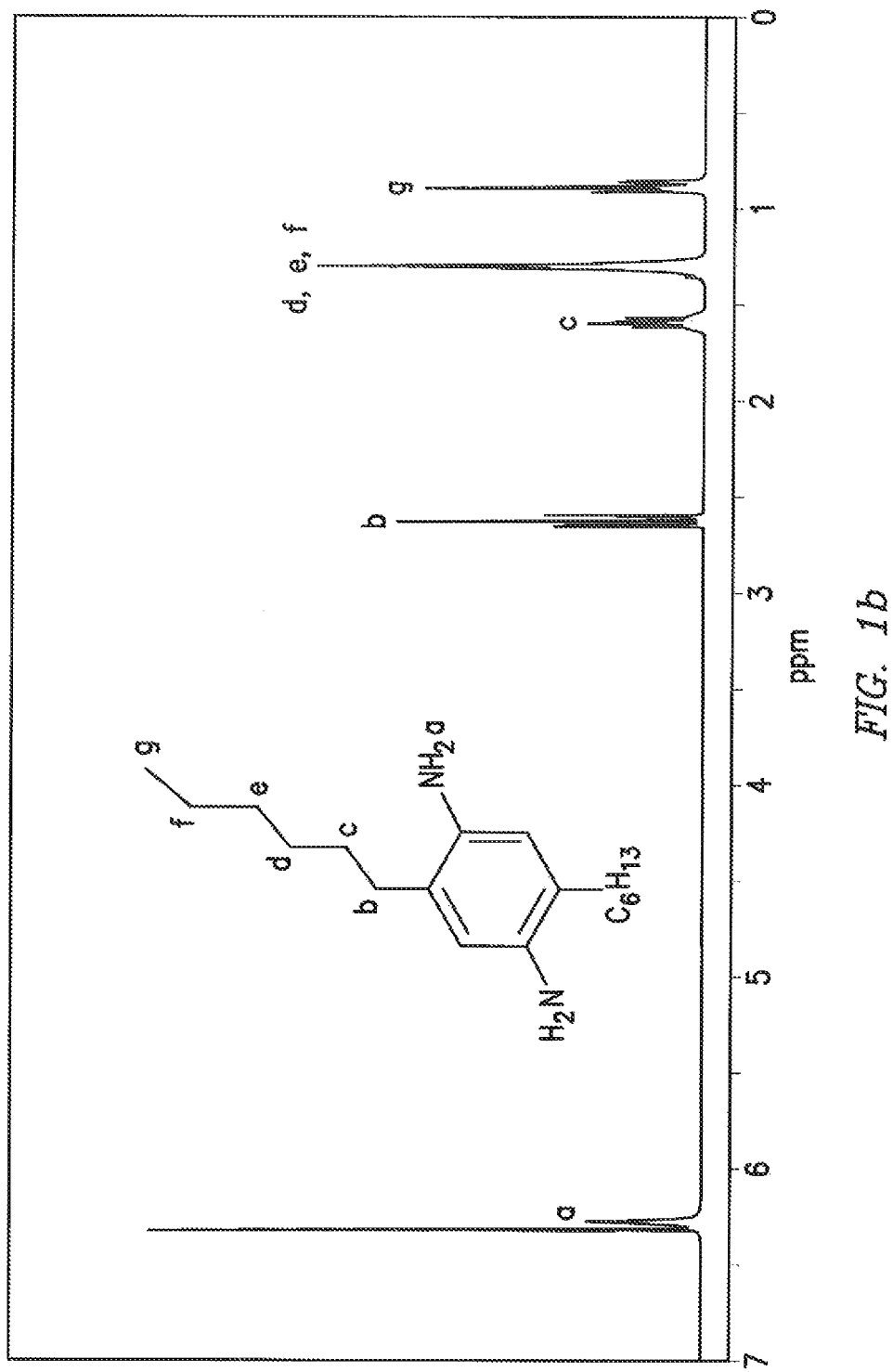
FIG. 1*b* depicts a ChemDraw-simulated $^1$H NMR spectrum of 2,5-dihyxylbenzene-1,4-diamine.asd

FIG. 1b depicts a ChemDraw-simulated ¹H NMR spectrum of 2,5-dihyxylbenzene-1,4-diamine.

Figure 2A:
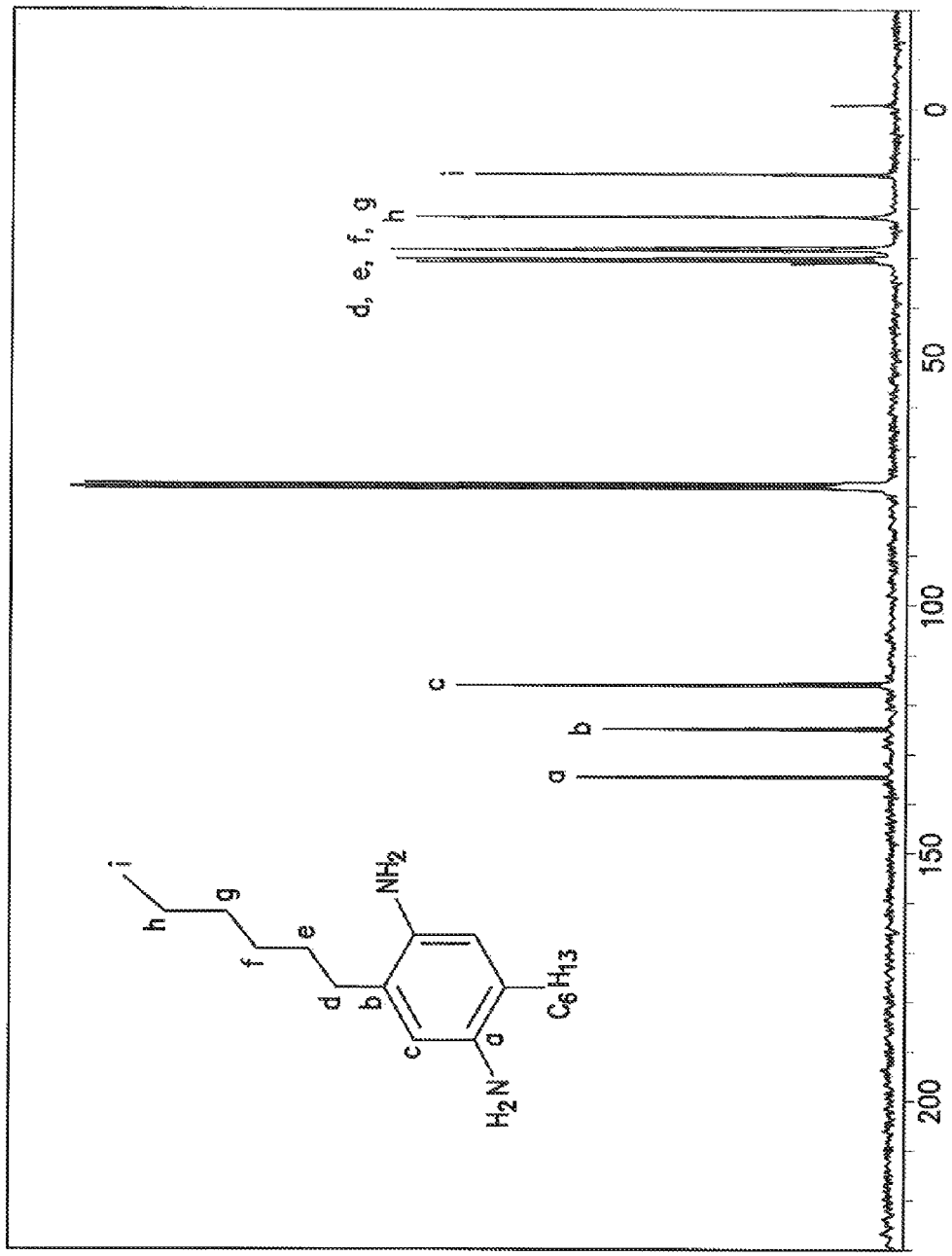
FIG. 2*a* depicts a $^{13}$C NMR spectrum of 2,5-dihyxylbenzene-1,4-diamine in CDCl3.

FIG. 2a depicts a ¹³C NMR spectrum of 2,5-dihyxylbenzene-1,4-diamine in CDCl₃.

Figure 2B:
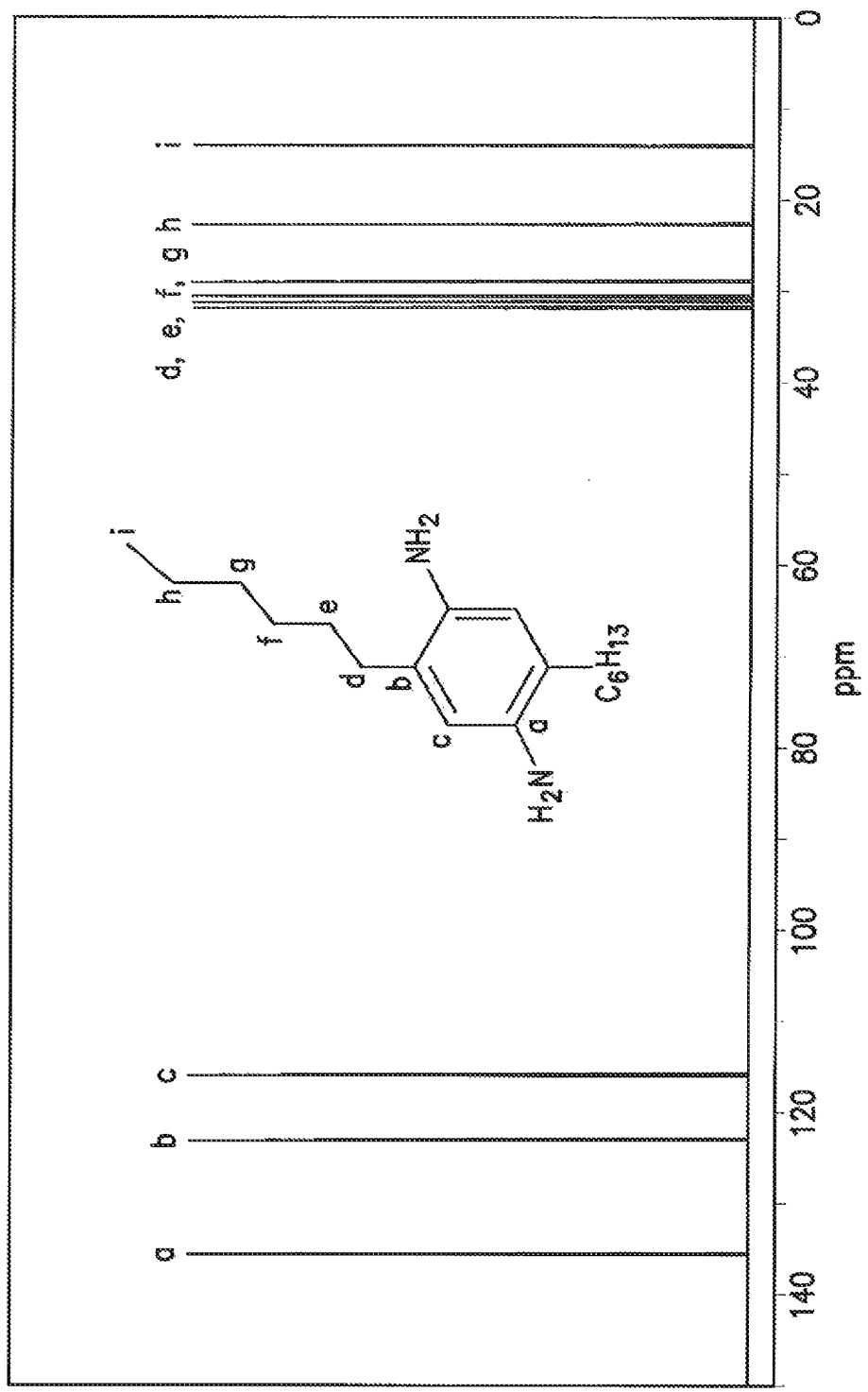
FIG. 2*b* depicts a ChemDraw-simulated $^{13}$C NMR spectrum of 2,5-dihyxylbenzene-1,4-diamine.

FIG. 2b depicts a ChemDraw-simulated ¹³C NMR spectrum of 2,5-dihyxylbenzene-1,4-diamine.

Example 2

Preparation of N,N'-(((2,5-dihexyl-1,4-phenylene)bis(azanediyl))bis(carbonothioyl))dibenzamide from 2,5-dihyxylbenzene-1,4-diamine Benzoyl chloride (100 mg, 0.08 mL) was added dropwise by syringe to a solution of $NH_4SCN$ (61 mg, 0.80 mmol) in dry acetone (50 mL). The mixture was stiffed at reflux temperature (60° C.) for 20 minutes. Afterwards, an acetone (20 mL) solution of 2,5-dihexylbenzene-1,4-diamine (76 mg, 0.28 mmol) was added by syringe. The mixture was refluxed for another 2 hours before it was cooled to room temperature. The mixture was poured into ice and stirred for 30 minutes. The precipitate was filtered and washed with water (50 mL) and dried in air. The solid was re-dissolved in THF (100 mL) to give a light yellow solution. A saturated aqueous solution of KOH (10 mL) was added dropwise. The solution changed the color from light yellow through greenish yellow to clear light yellow solution. After 30 minutes, the solution was poured into an aqueous HCL solution (3.6 M, 100 mL) with ice. Ammonium aqueous solution was added dropwise to reach a pH of 10. The precipitate was filtered and dried in air (yield: 100 mg, 73%).

Figure 3A:
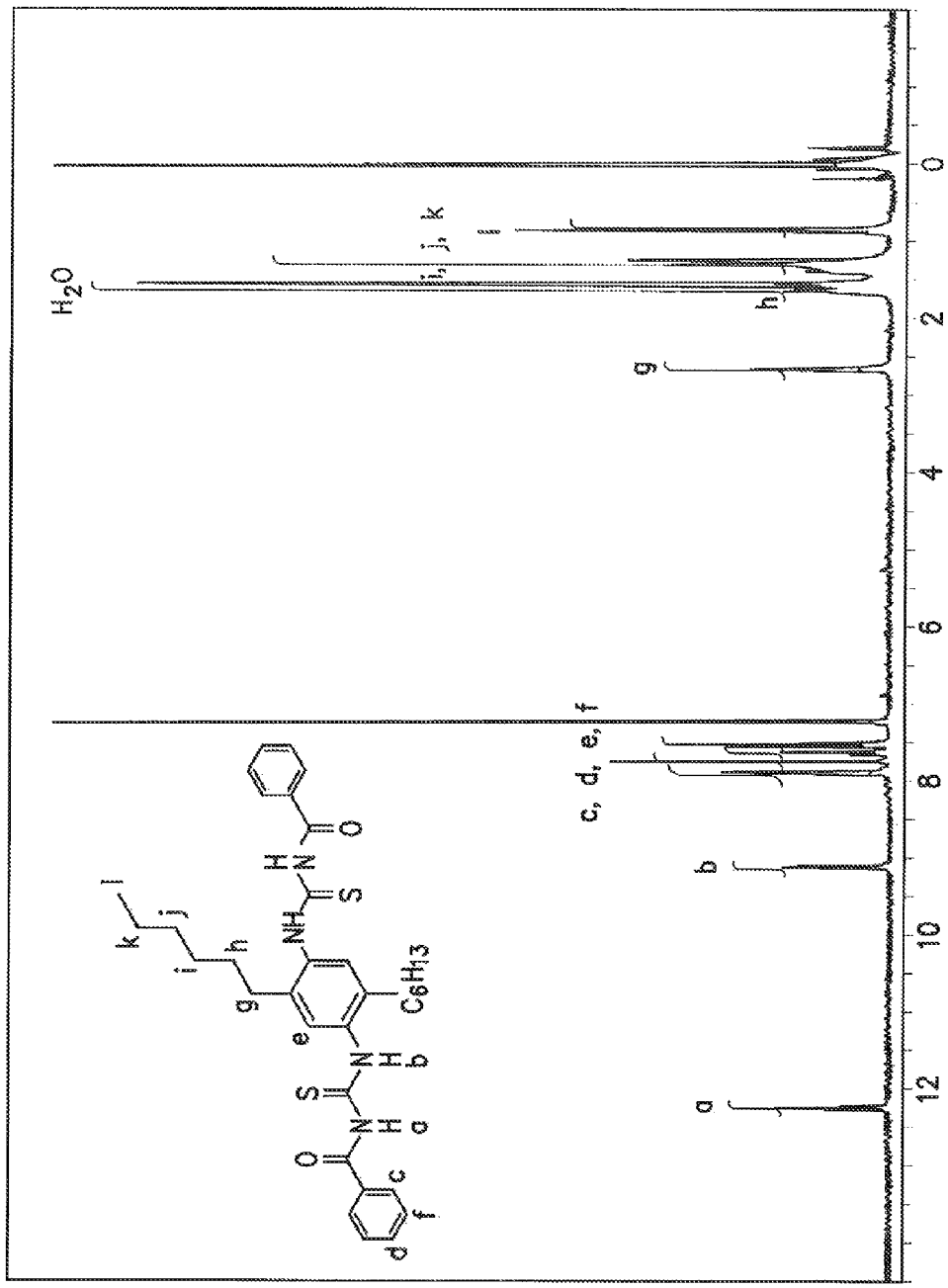
FIG. 3*a* depicts a $^1$H NMR spectrum of N,N'-(((2,5-dihexyl-1,4-phenylene)bis(azanediyl))bis(carbonothioyl))dibenzamide in CDCl$_3$.

FIG. 3a depicts as $^1H$ NMR spectrum of N,N'-(((2,5-dihexyl-1,4-phenylene)bis(azanediyl))bis(carbonothioyl))dibenzamide in $CDCl_3$.

Figure 3B:
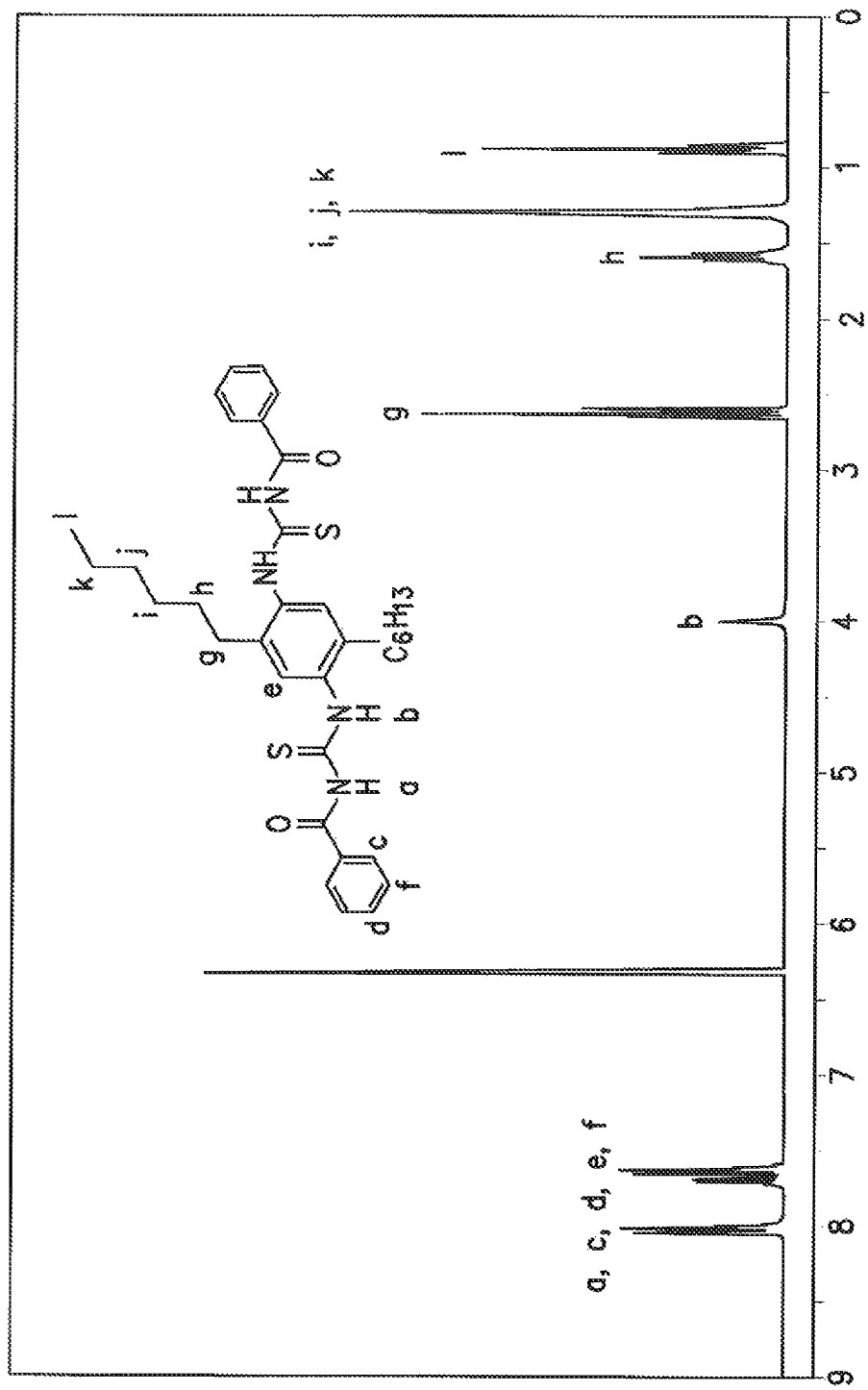
FIG. 3*b* depicts a ChemDraw-simulated $^1$H NMR spectrum of N,N'-(((2, 5-dihexyl-1,4-phenylene)bis(azanediyl))bis(carbonothioyl))dibenzamide.

FIG. 3b depicts a ChemDraw-simulated $^1H$ NMR spectrum of N,N'-(((2, 5-dihexyl-1,4-phenylene)bis(azanediyl)bis(carbonothioyl))dibenzamide.

Figure 4:
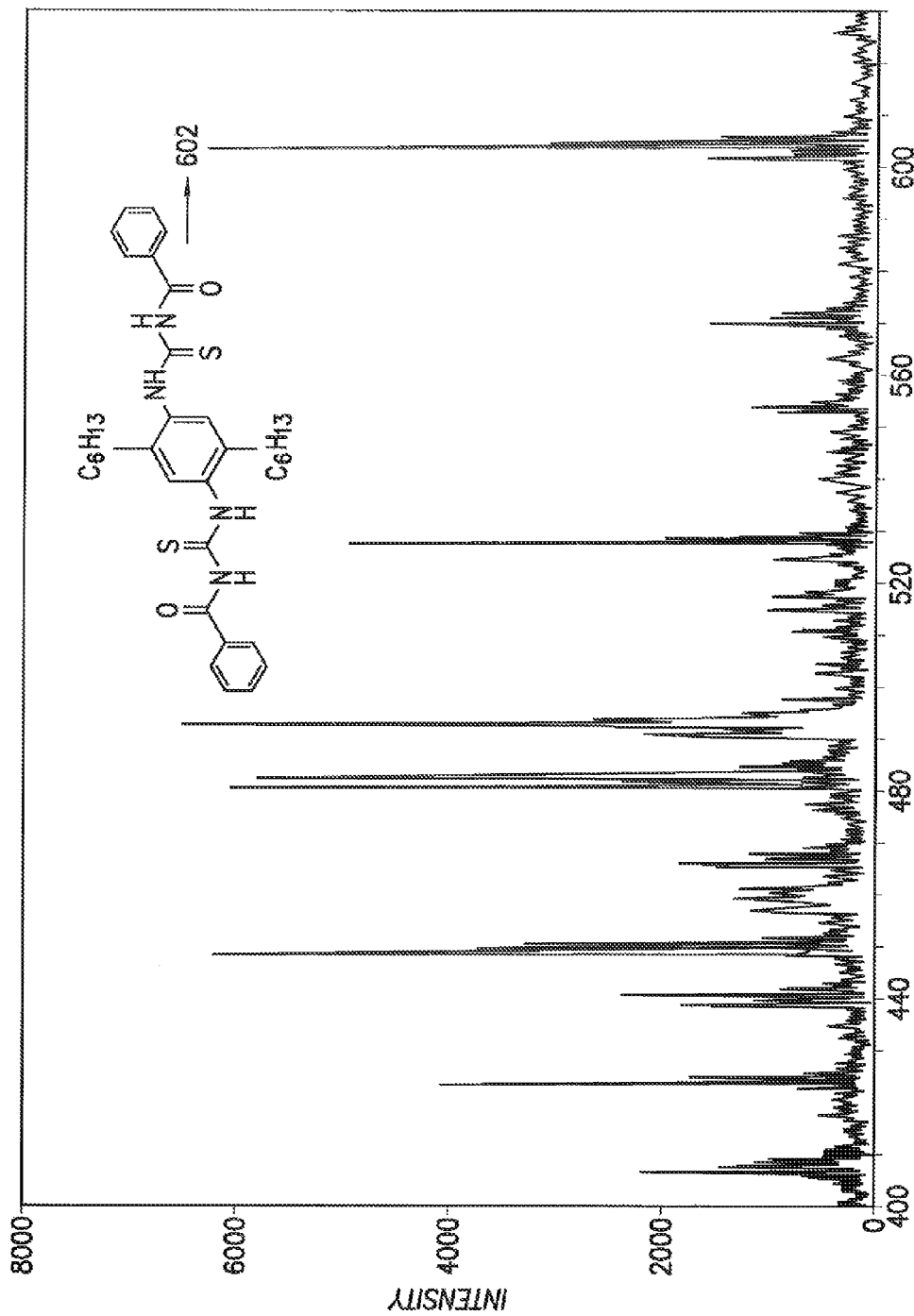
FIG. 4 depicts a matrix-assisted laser desorption ionization-time-of-flight mass spectrometry (MALDI-TOF MS) spectrum of N,N'-(((2,5-dihexyl-1,4-phenylene)bis(azanediyl))bis(carbonothioyl))dibenzamide.

FIG. 4 depicts a matrix-assisted laser desorption ionization-time-of-flight mass spectrometry (MALDI-TOF MS) spectrum of N,N'-(((2,5-dihexyl-1,4-phenylene)bis(azanediyl))bis(carbonothioyl))dibenzamide.

Example 3

Preparation of 1,1'-(2,5-dihexyl-1,4-phenylene)bis(thiourea) from N,N'-(((2,5-dihexyl-1,4-phenylene)bis(azanediyl))bis(carbonothioyl))dibenzamide Aqueous HCl (31 mL) was added to an ethanol (50 mL) suspension of 2,5-dihyxylbenzene-1,4-diamine (3.5 g, 12.7 mmol) at room temperature. The mixture was heated at 50° C. for 1 day. Ammonium thiocyanate (3.8 g, 50 mmol) was added to the mixture. The mixture was then heated at 100° C. for another day. The mixture was cooled to room temperature and filtered. The solid was dried in air (yield: 2.0 g).

Example 4

Preparation of 1,1'-(2,5-dihexyl-1,4-phenylene)bis(thiourea) from N,N'-(((2,5-dihexyl-1,4-phenylene)bis(azanediyl))bis(carbonothioyl))dibenzamide N,N'-(((2,5-dihexyl-1,4-phenylene)bis(azanediyl)bis(carbonothioyl))dibenzamide (100 mg, 0.17 mmol) was re-dissolved in THF (100 mL). A saturated aqueous solution of KOH (10 mL) was added dropwise. After 30 minutes, the solution was poured into an aqueous HCL solution (3.6 M, 100 mL) with ice. Ammonium aqueous solution was added dropwise to reach a pH of 10. The precipitate was filtered and dried in air (yield; 33 mg, 50%).

Figure 5A:
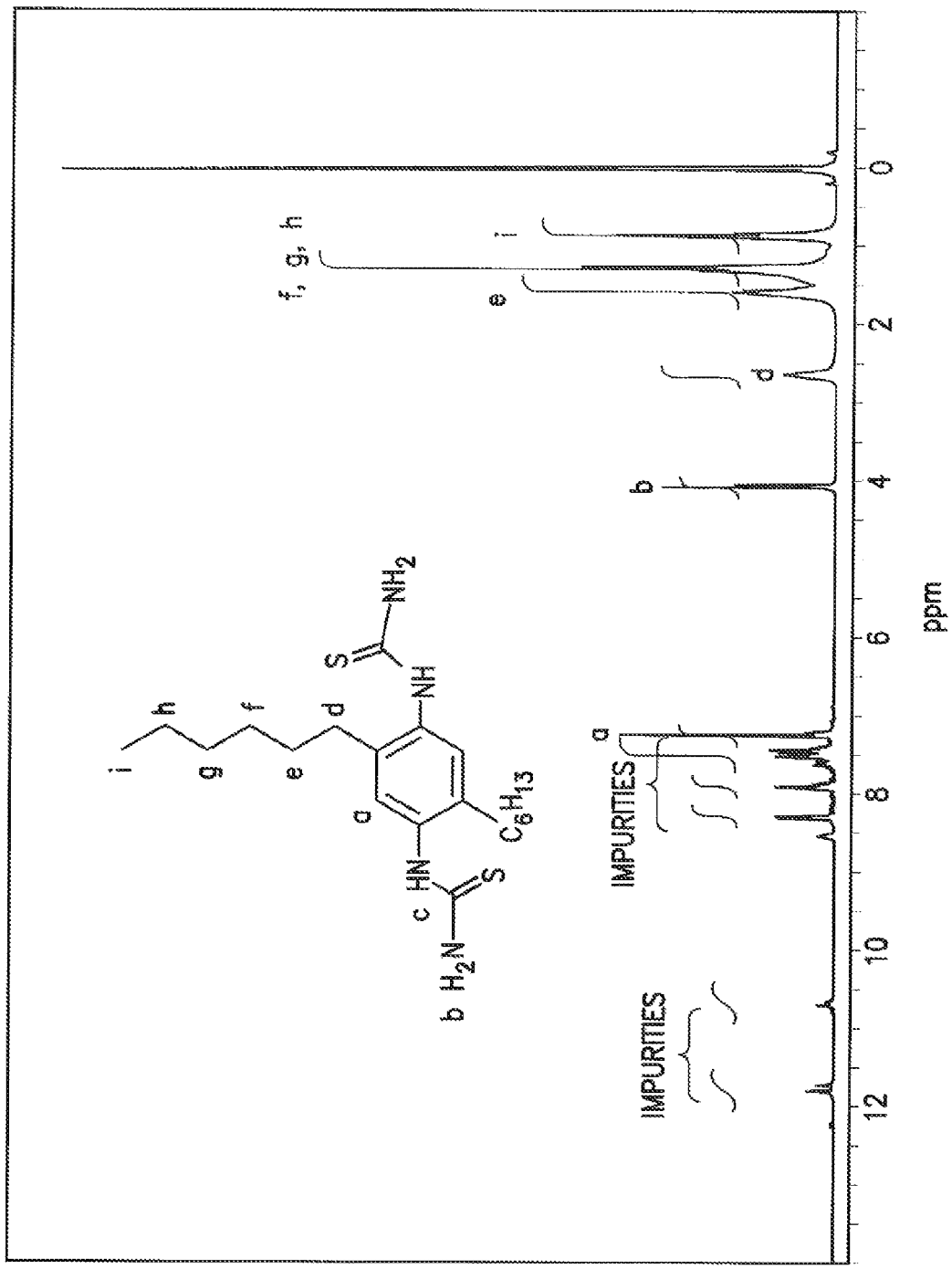
FIG. 5*a* depicts a $^1$H NMR spectrum of 1,1'-(2,5-dihexyl-1,4-phenylene)bis(thiourea) in CDCl$_3$.

FIG. 5a depicts a $^1H$ NMR spectrum of 1,1'-(2,5-dihexyl-1,4-phenylene)bis(thiourea) in $CDCl_3$.

Figure 5B:
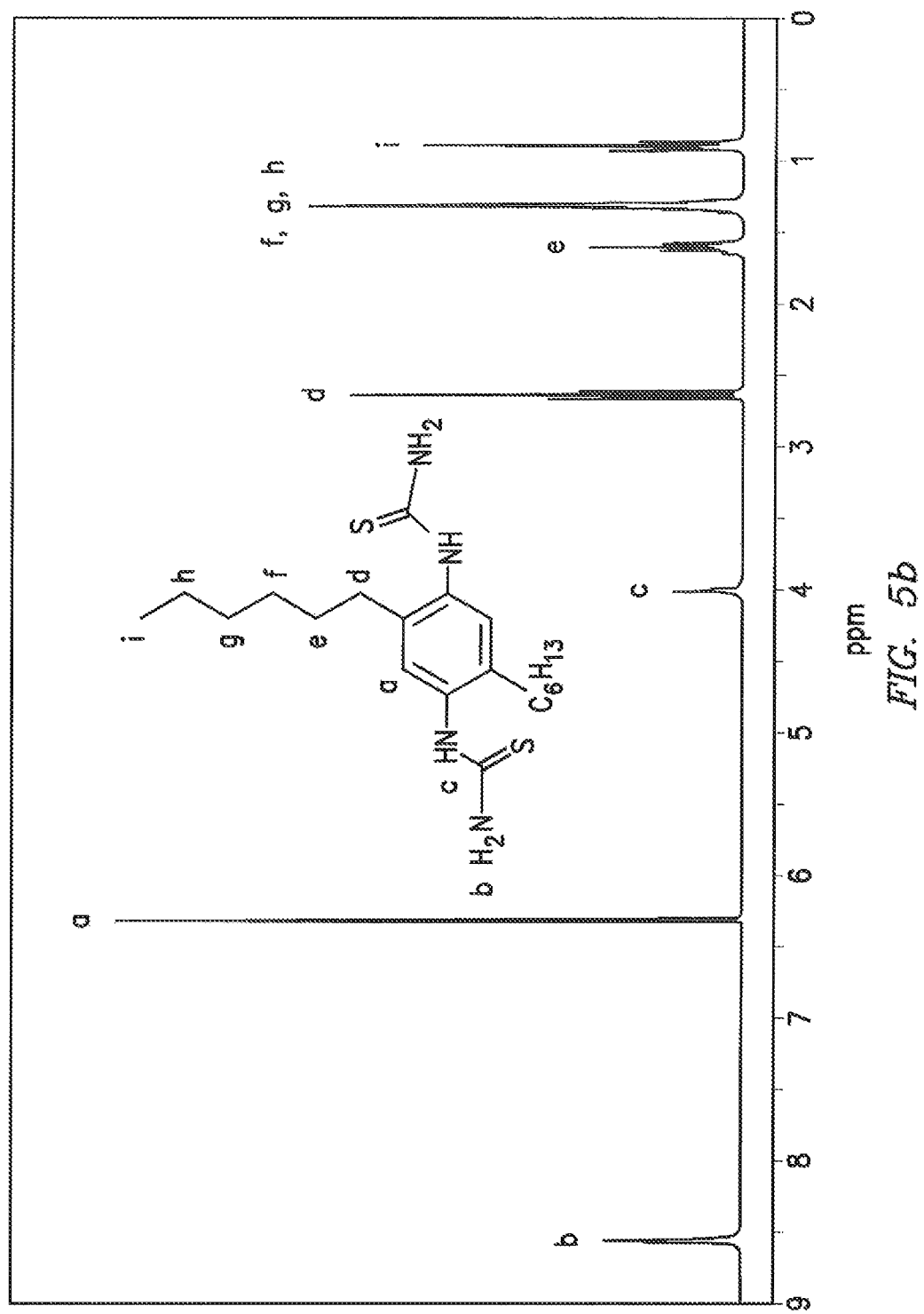
FIG. 5*b* depicts a ChemDraw-simulated $^1$H NMR spectrum of 1,1'-(2,5-dihexyl-1,4-phenylene)bis(thiourea).

FIG. 5b depicts a ChemDraw-simulated $^1H$ NMR spectrum of 1,1'-(2,5-dihexyl-1,4-phenylene)bis(thiourea).

Example 5

Preparation of 4,8-dihexylbenzo[1,2-d:4,5-d']bis(thiazole)-2,6-diamine from 1,1'-(2,5-dihexyl-1,4-phenylene)bis(thiourea)

An anhydrous CHCl3 solution (150 mL) of $Br_2$ (1.92 g, 12 mmol) was added to an anhydrous $CHCl_3$ (200 mL) solution, 1,1'-(2,5-dihexyl-1,4-phenylene)bis(thiourea) at room temperature dropwise over a period of 30 minutes by using an addition funnel. The mixture slowly turned to red-orange while being stirred for 24 hours. The mixture was then refluxed at 60° C. for 24 hours. After refluxing, the mixture turned yellow-orange. The reaction mixture was cooled to room temperature and then washed with an aqueous sodium bisulfite solution (50 mL) by using a separation funnel. The organic layer was separated, and the solvent was removed under reduced pressure. The yellow solid was washed with concentrated aqueous ammonium and water. Afterward, the solid was recrystallized from glacial acetic acid to give a light yellow solid (yield: 2 g, 80%).

Figure 6A:
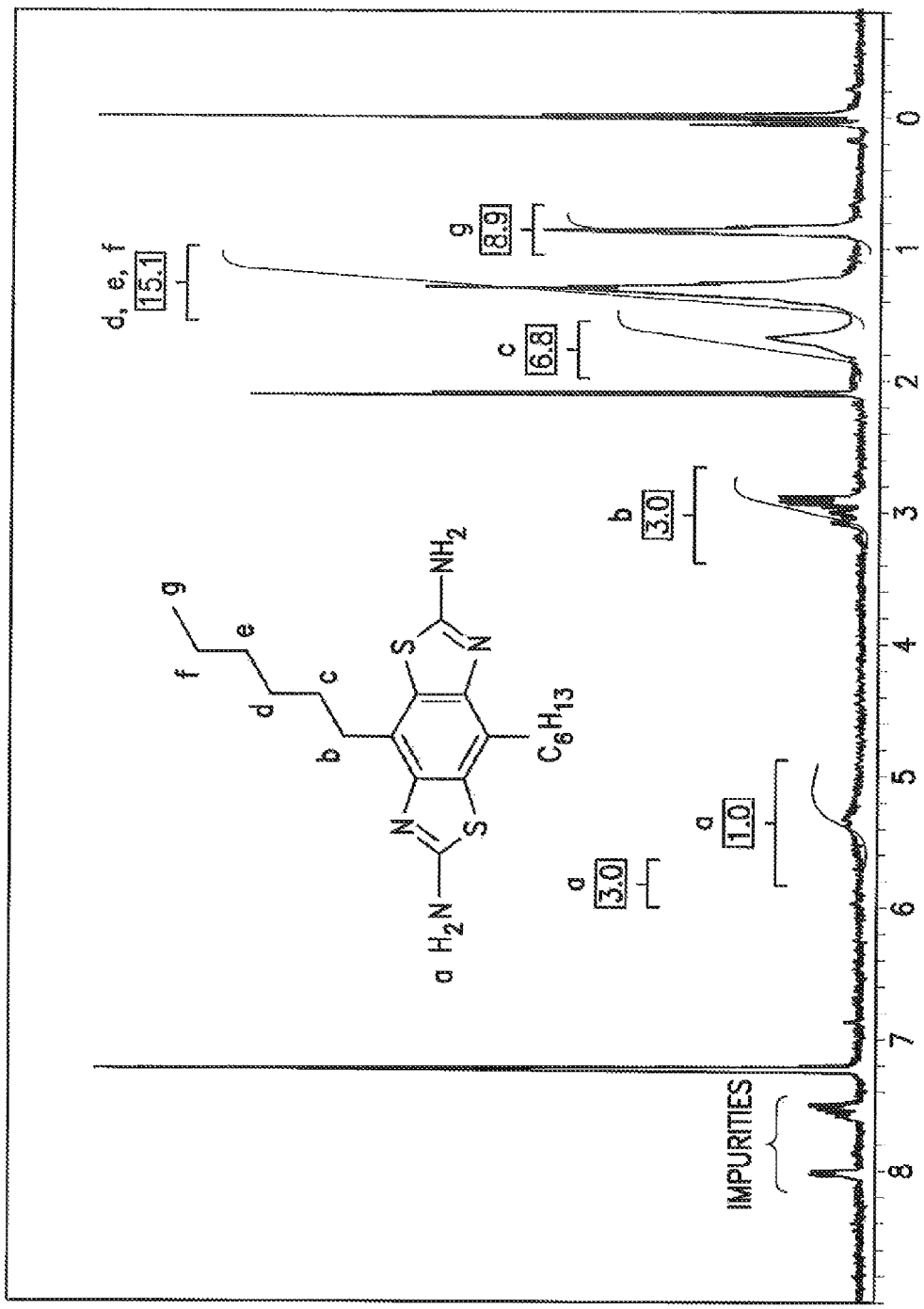
FIG. 6*a* depicts a $^1$H NMR spectrum of 4,8-dihexylbenzo[1,2-d:4,5-d']bis(thiazole)-2,6-diamine in CDCl$_3$.

FIG. 6a depicts a $^1H$ NMR spectrum of 4,8-dihexylbenzo[1,2-d:4,5-d']bis(thiazole)-2,6-diamine in $CDCl_3$.

Figure 6B:
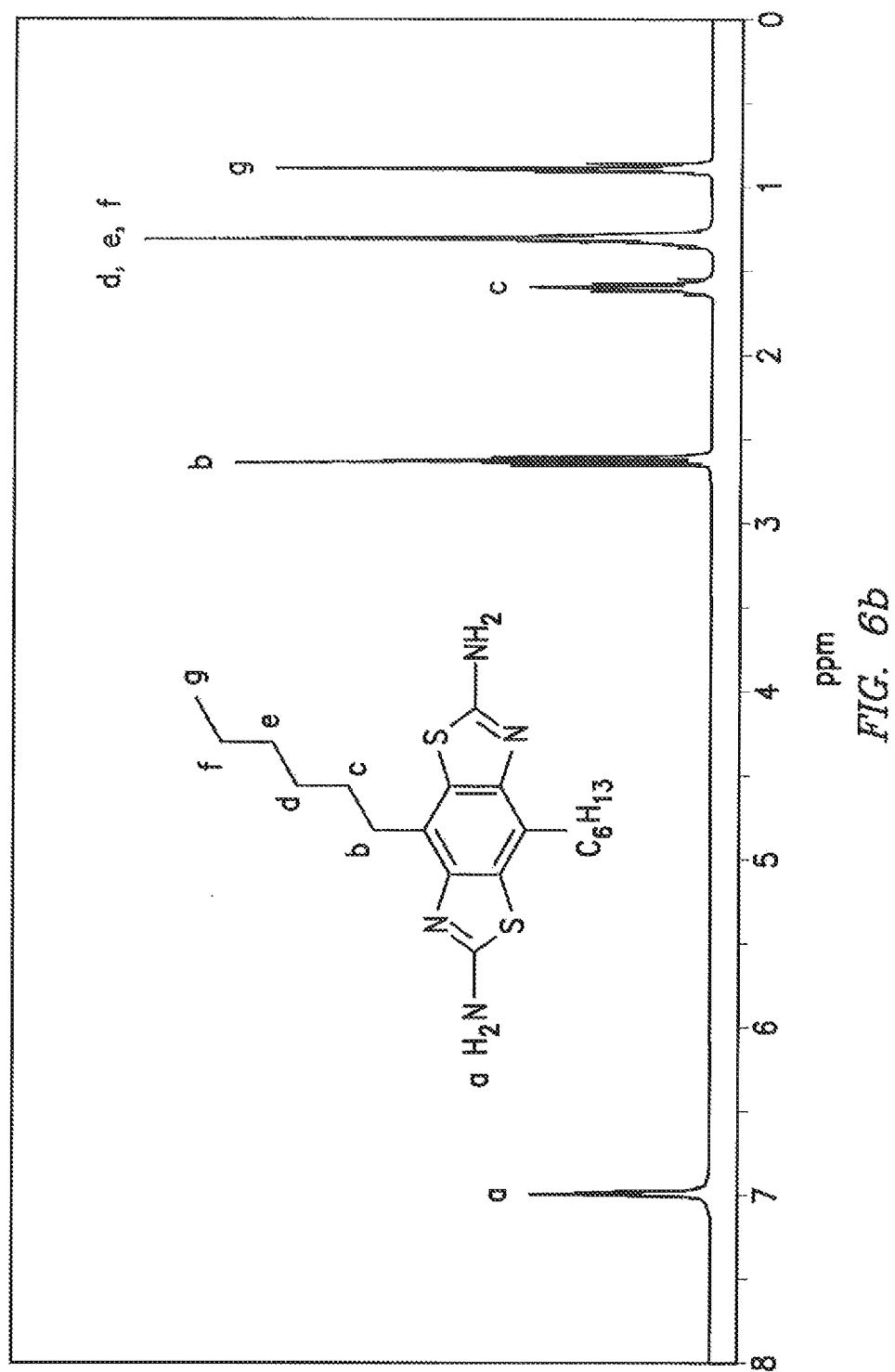
FIG. 6*b* depicts a ChemDraw-simulated $^1$H NMR spectrum of 4,8-dihexylbenzo[1,2-d:4,5-d']bis(thiazole)-2,6-diamine.

FIG. 6b depicts a ChemDraw-simulated $^1H$ NMR spectrum of 4,8-dihexylbenzo[1,2-d:4,5-d']bis(thiazole)-2,6-diamine.

Figure 7:
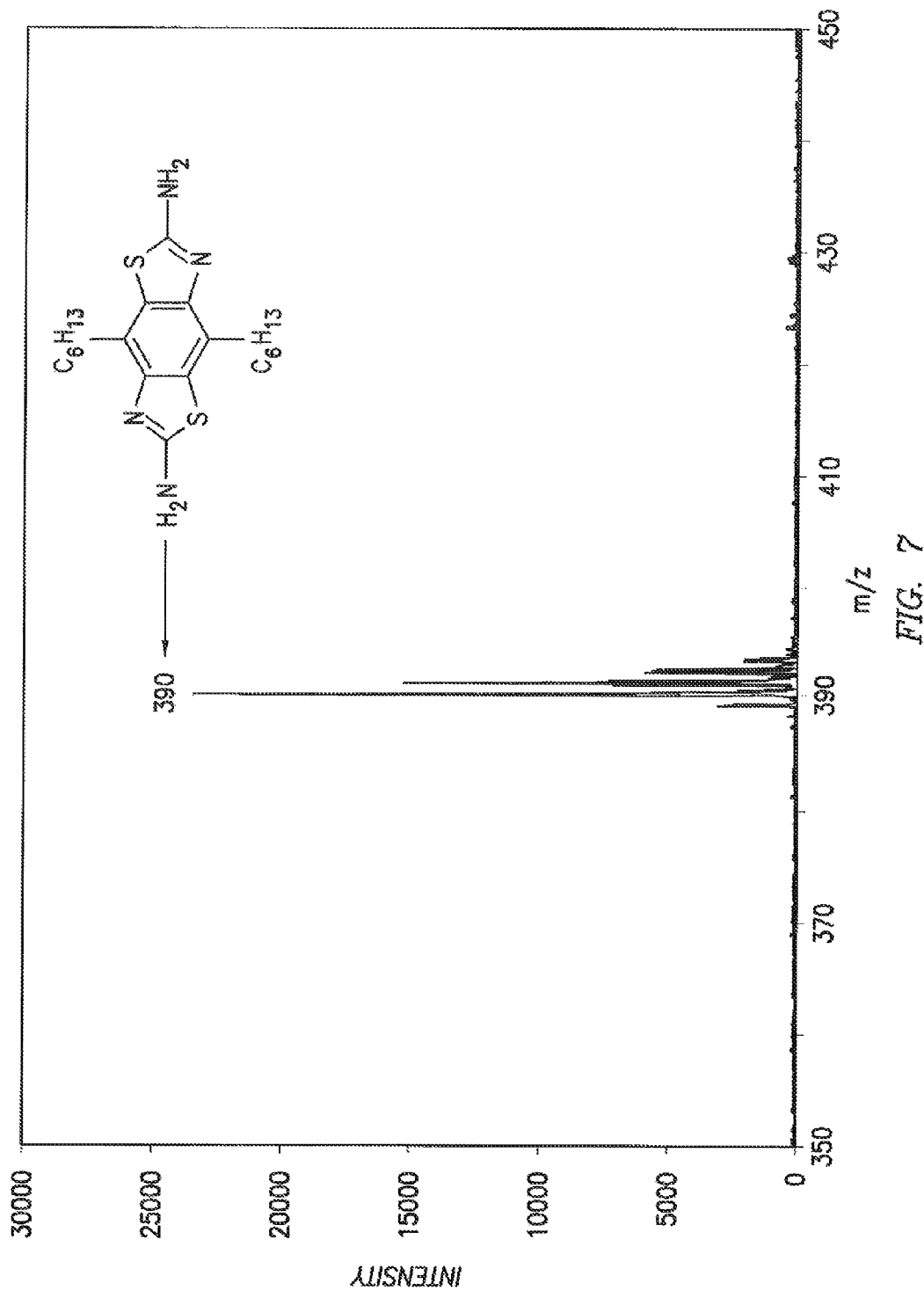
FIG. 7 depicts a MALDI-TOF MS spectrum of 4,8-dihexylbenzo[1,2-d:4,5-d']bis(thiazole)-2,6-diamine.

FIG. 7 depicts a MALDI-TOF MS spectrum of 4,8-dihexylbenzo[1,2-d:4,5-d']bis(thiazole)-2,6-diamine.

Example 6

Preparation of 2,6-dibromo-4,8-dihexylbenzo[1,2-d:4,5-d']bis(thiazole) from 4,8-dihexylbenzo[1,2-d:4,5-d']bis(thiazole)-2,6-diamine A t-butyl nitrite liquid (31 mg, 0.3 mmol) was added to an anhydrous $CH_3CN$ (40 mL) of $CuBr_2$ (54 mg, 0.24 mmol). A solid of 4,8-dihexylbenzo[1,2-d:4,5-d']bis(thiazole)-2,6-diamine (78 mg, 0.2 mmol) was added to the mixture portionwise. The mixture was then refluxed at 65° C. for 1 hour. Afterward, the reaction mixture was cooled and then poured into aqueous hydrochloric acid (20%, 200 mL) and extracted with $CH_2Cl_2$ (150 mL). The organic solution was dried over anhydrous magnesium sulfate. After filtration, the solvent was removed under reduced pressure to give a dark solid, which was purified by column chromatography (silica gel, toluene) to provide the product as a light red crystalline solid (yield: 51 mg, 50%).

Figure 8A:
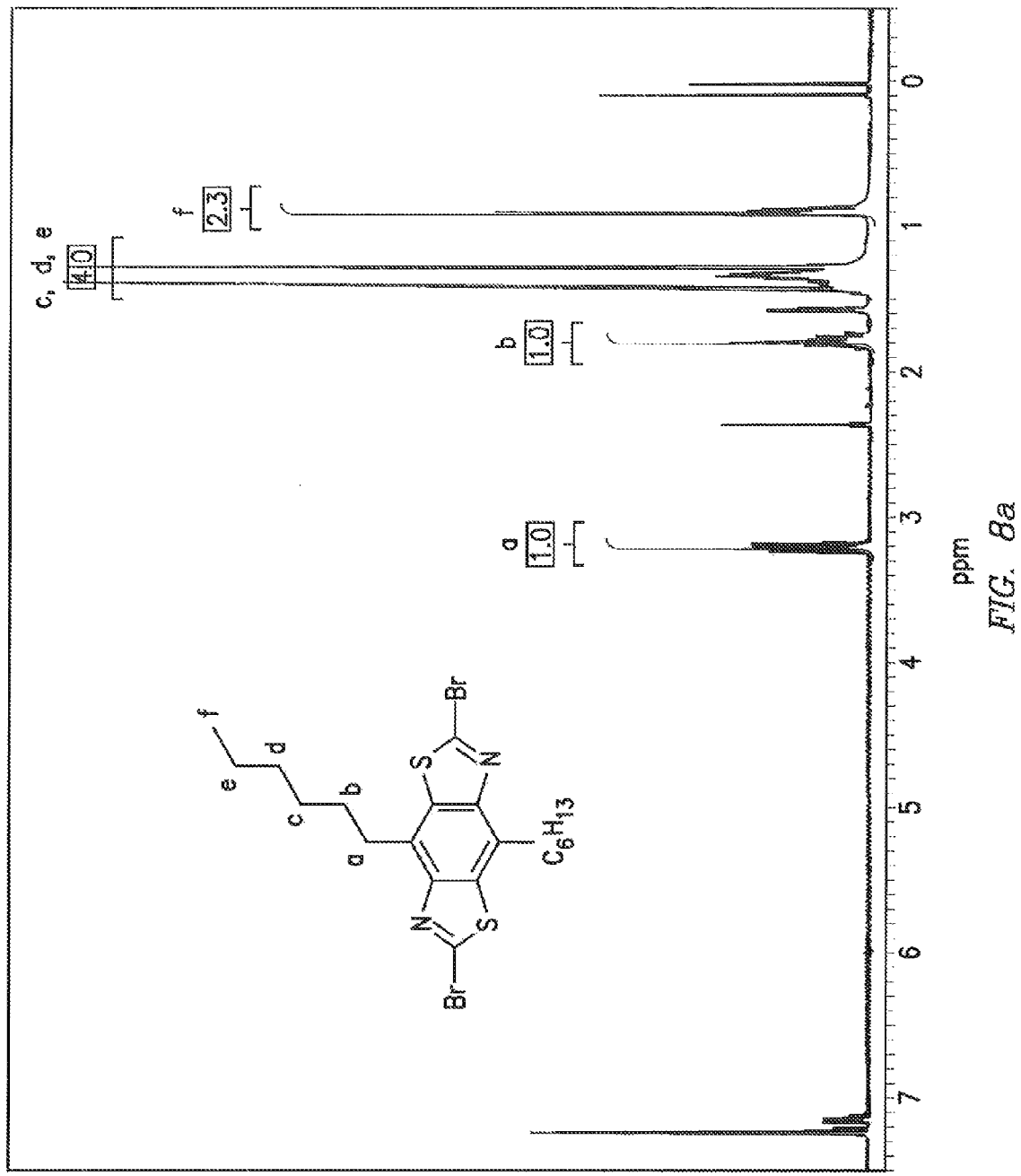
FIG. 8*a* depicts a $^1$H NMR spectrum of 2,6-dibromo-4,8-dihexylbenzo[1,2-d:4,5-d']bis(thiazole) in CDCl$_3$.

FIG. 8a depicts a $^1H$ NMR spectrum of 2,6-dibromo-4,8-dihexylbenzo[1,2-d:4, 5-d']bis(thiazole) in $CDCl_3$.

Figure 8B:
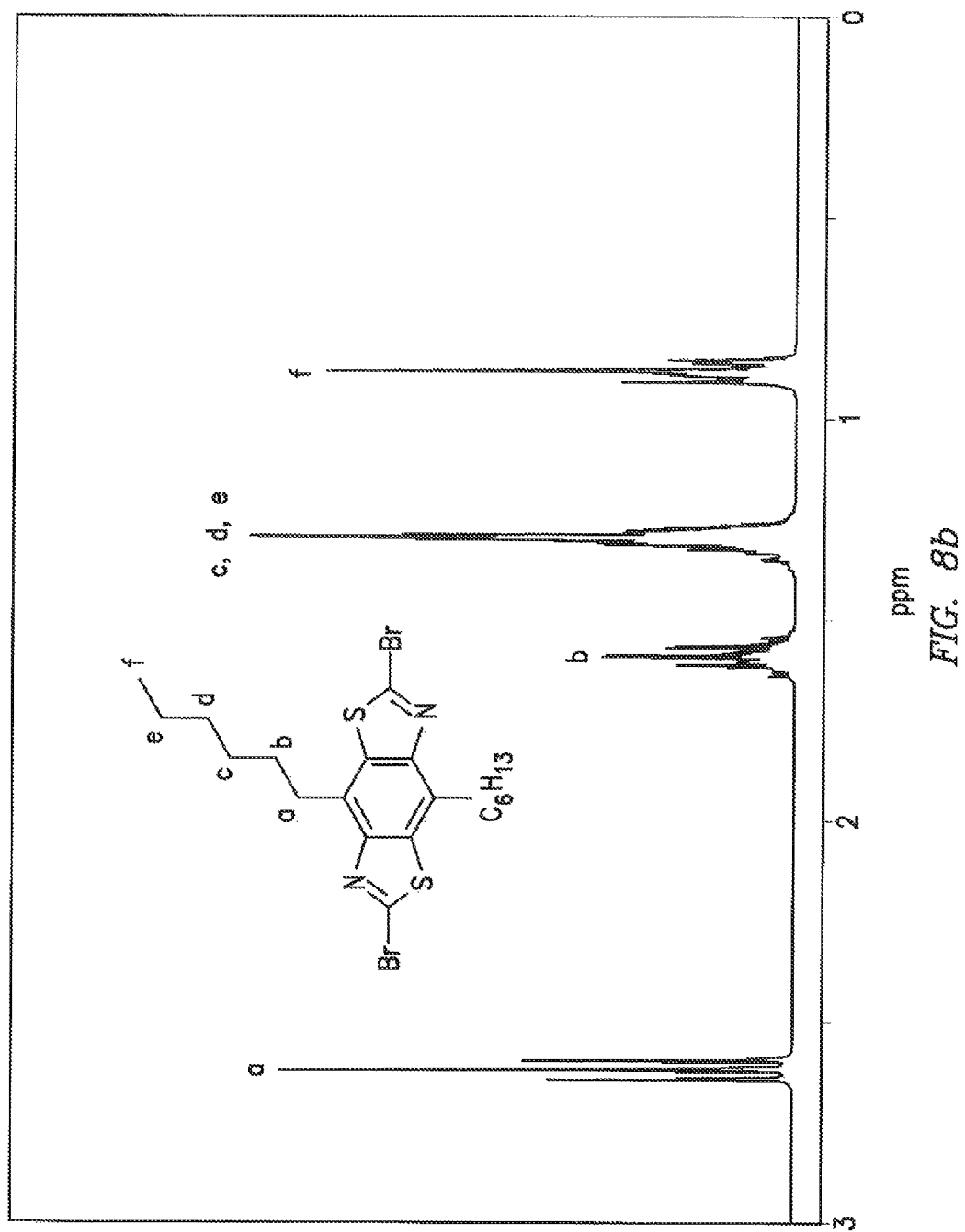
FIG. 8b depicts a ChemDraw-simulated ¹H NMR spectrum of 2,6-dibromo-4,8-dihexylbenzo[1,2-d:4,5-d']bis(thiazole).

FIG. 8b depicts a ChemDraw-simulated $^1H$ NMR spectrum of 2,6-dibromo-4,8-dihexylbenzo[1,2-d:4,5-d']bis(thiazole).

Figure 9A:
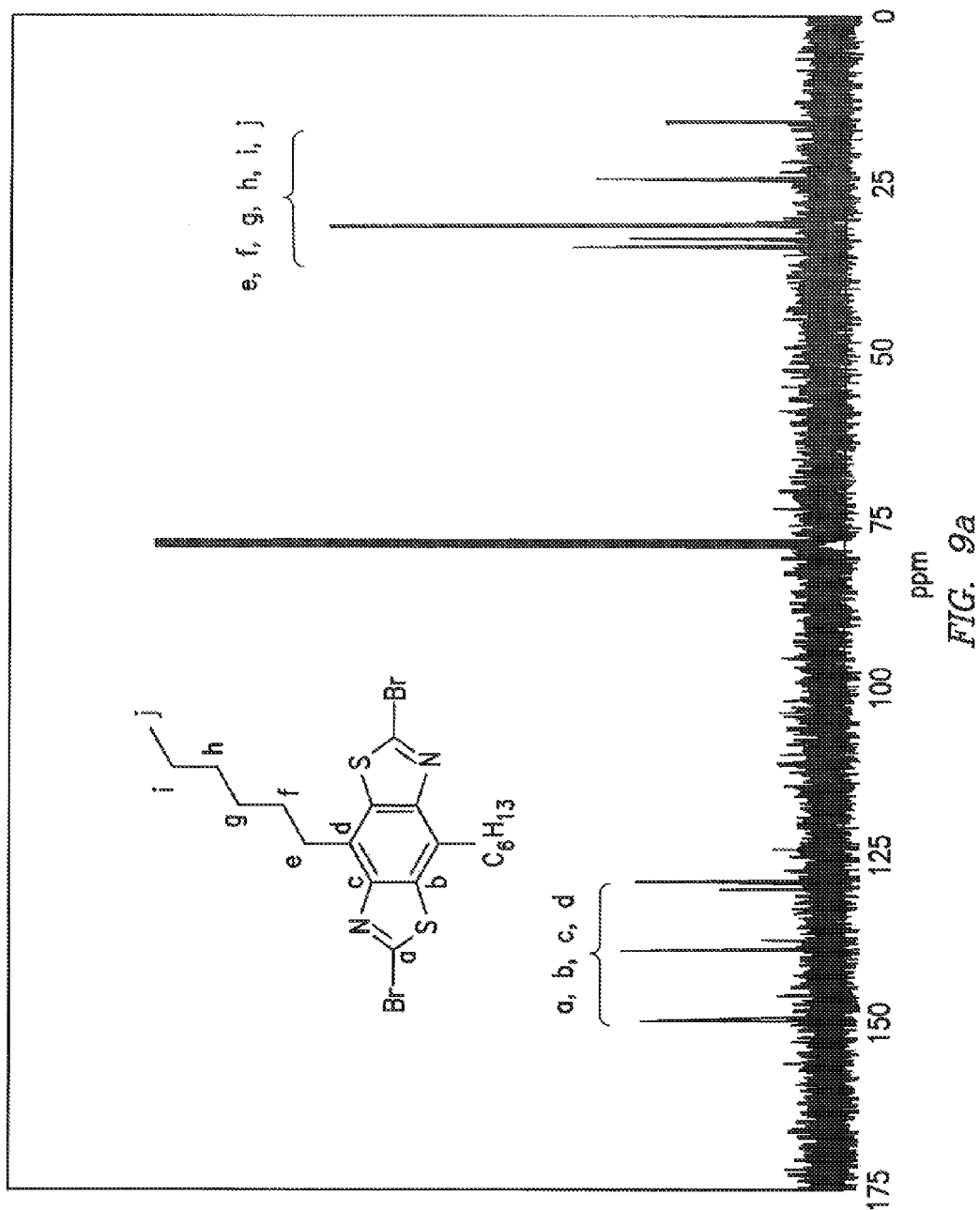
FIG. 9a depicts a ¹³C NMR spectrum of 2,6-dibromo-4,8-dihexylbenzo[1,2-d:4,5-d']bis(thiazole) in CDCl₃.
Figure 9B:
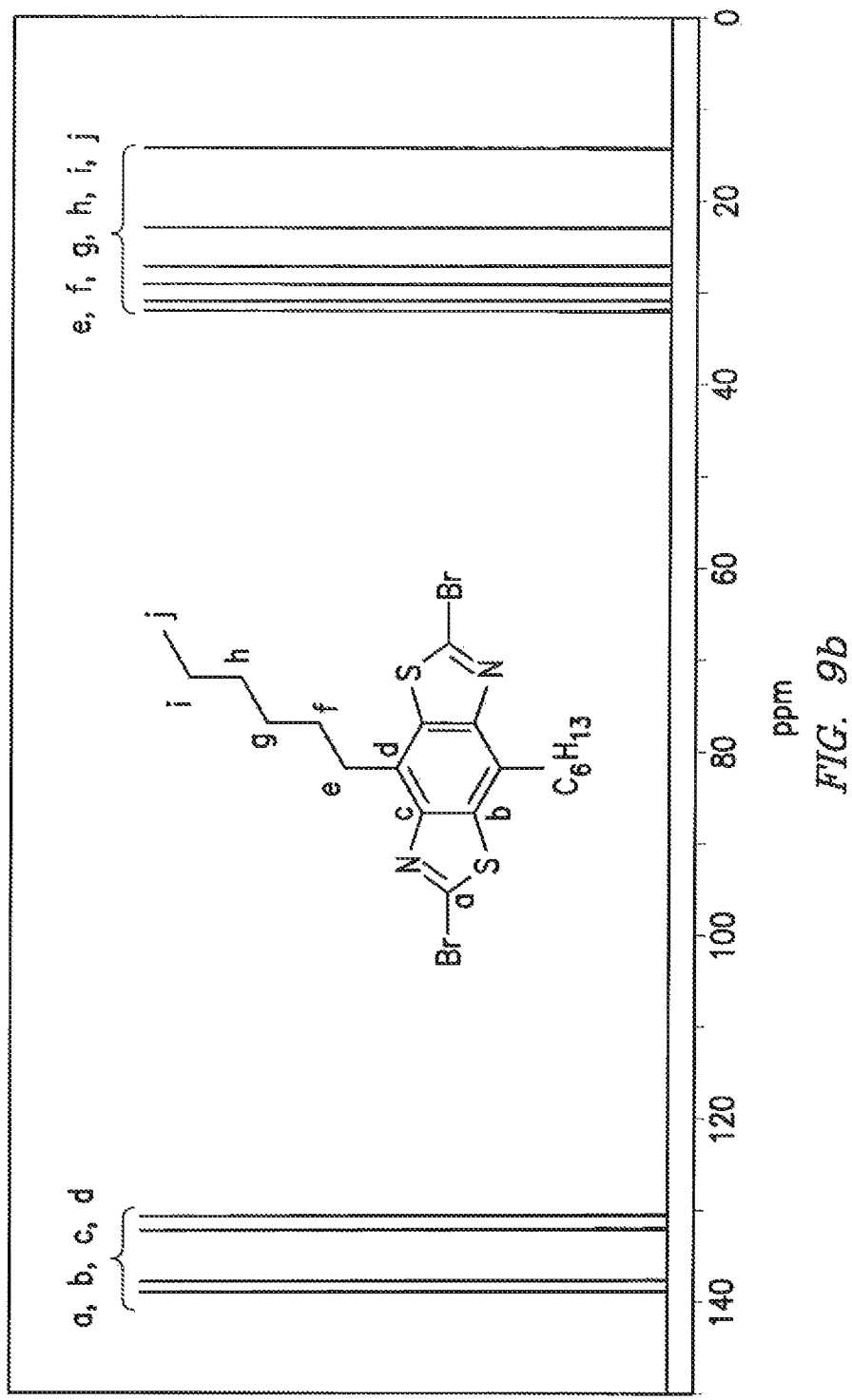
FIG. 9b depicts a ChemDraw-simulated ¹³C NMR spectrum of 2,6-dibromo-4,8-dihexylbenzo[1,2-d:4,5-d']bis(thiazole).

FIG. 9a depicts a $^{13}C$ NMR spectrum of 2,6-dibromo-4,8-dihexylbenzo[1,2-d:4, 5-d']bis(thiazole) in $CDCl_3$. FIG. 9b depicts a ChemDraw-simulated $^{13}C$ NMR spectrum of 2,6-dibromo-4,8-dihexylbenzo[1,2-d:4,5-d']bis(thiazole).

Figure 10:
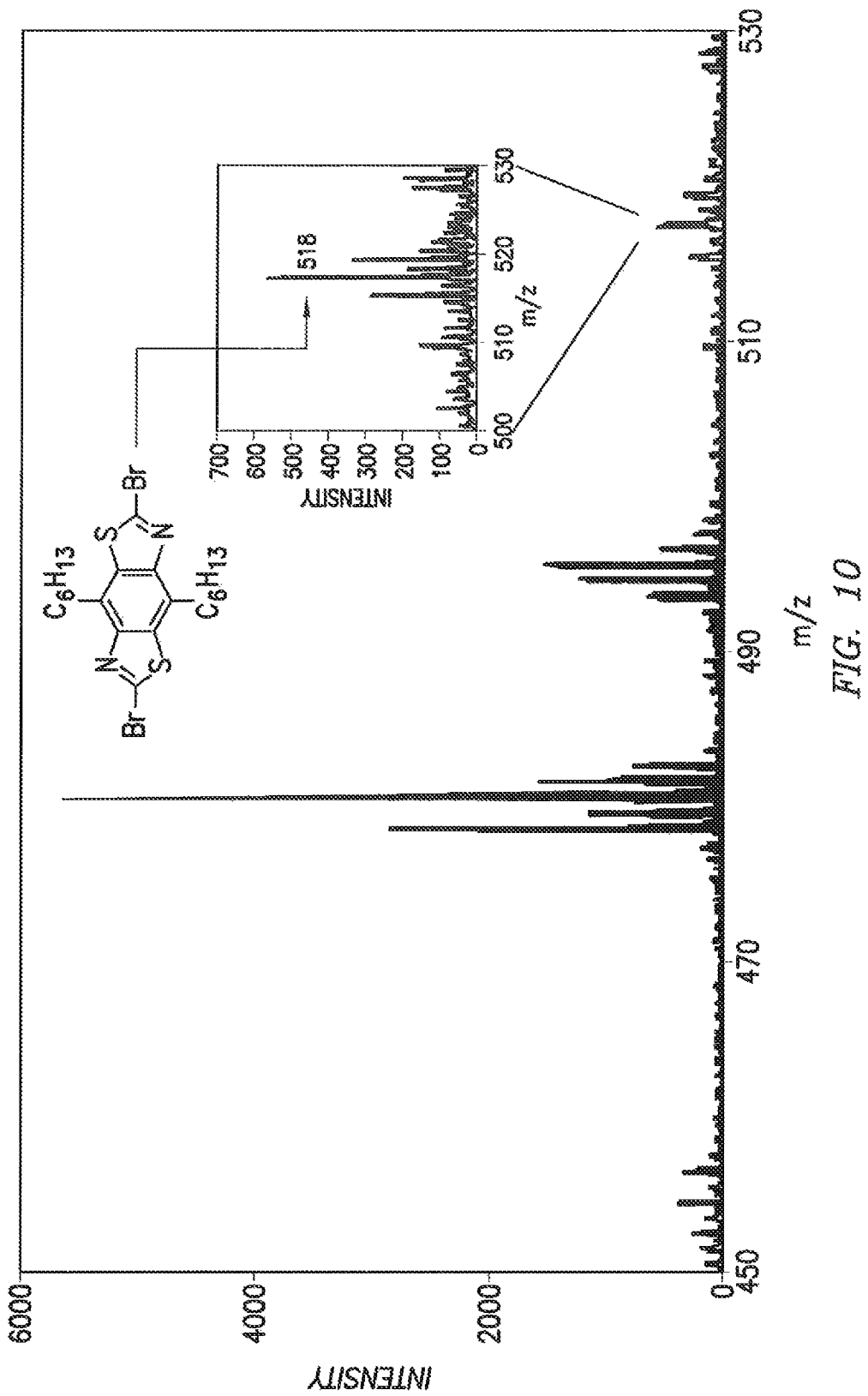
FIG. 10 depicts MALDI-TOF MS spectrum of 2,6-dibromo-4,8-dihexylbenzo[1,2-d:4,5-d']bis(thiazole).

FIG. 10 depicts MALDI-TOF MS spectrum of 2,6-dibromo-4,8-dihexylbenzo[1, 2-d:4,5-d']bis(thiazole).

Figure 11:
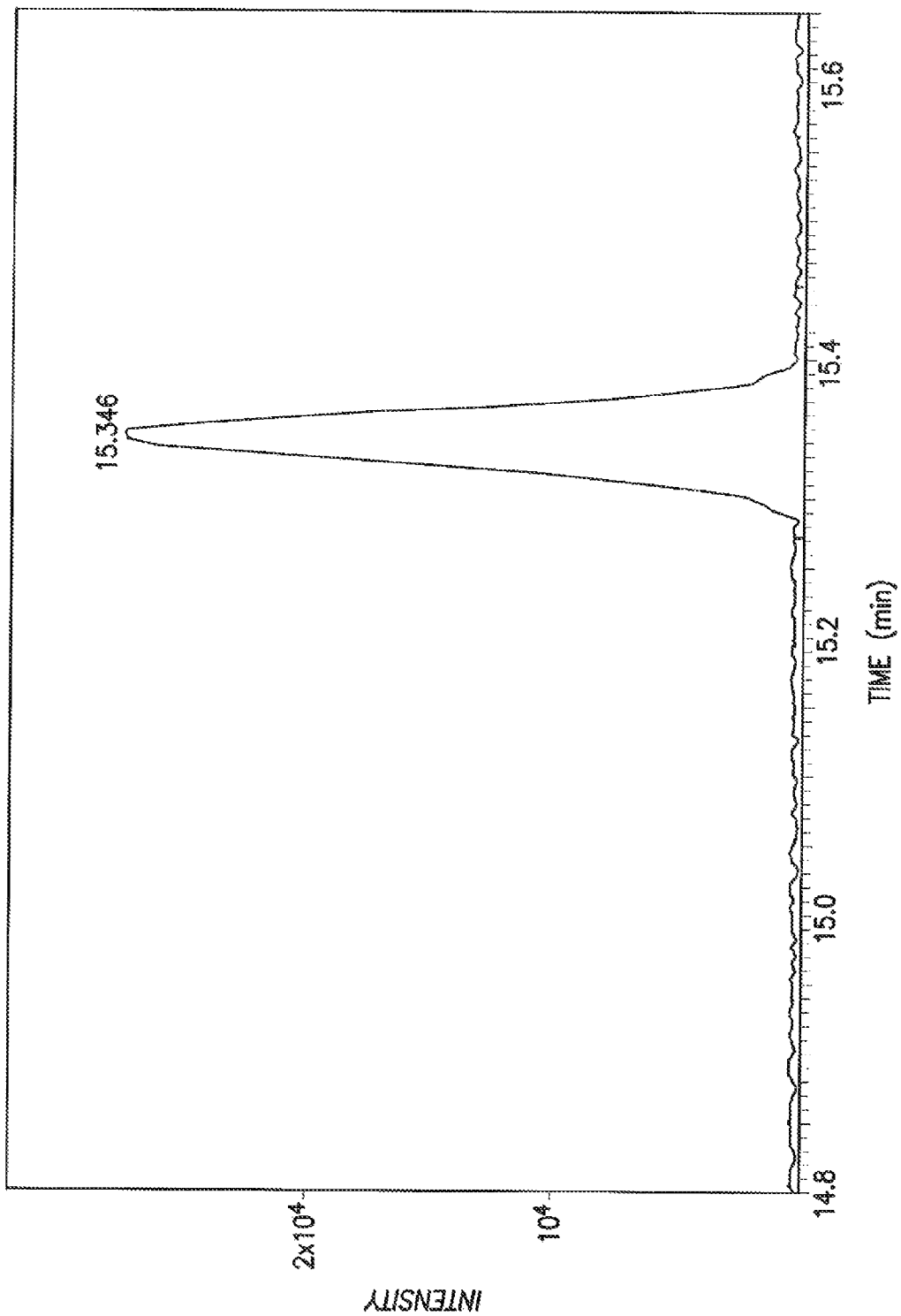
FIG. 11 depicts a gas chromotography analysis result of 2,6-dibromo-4,8-dihexylbenzo[1,2-d:4,5-d']bis(thiazole).

FIG. 11 depicts a gas chromatography analysis result of 2,6-dibromo-4,8-dihexylbenzo[1,2-d:4,5-d']bis(thiazole).

Figure 12:
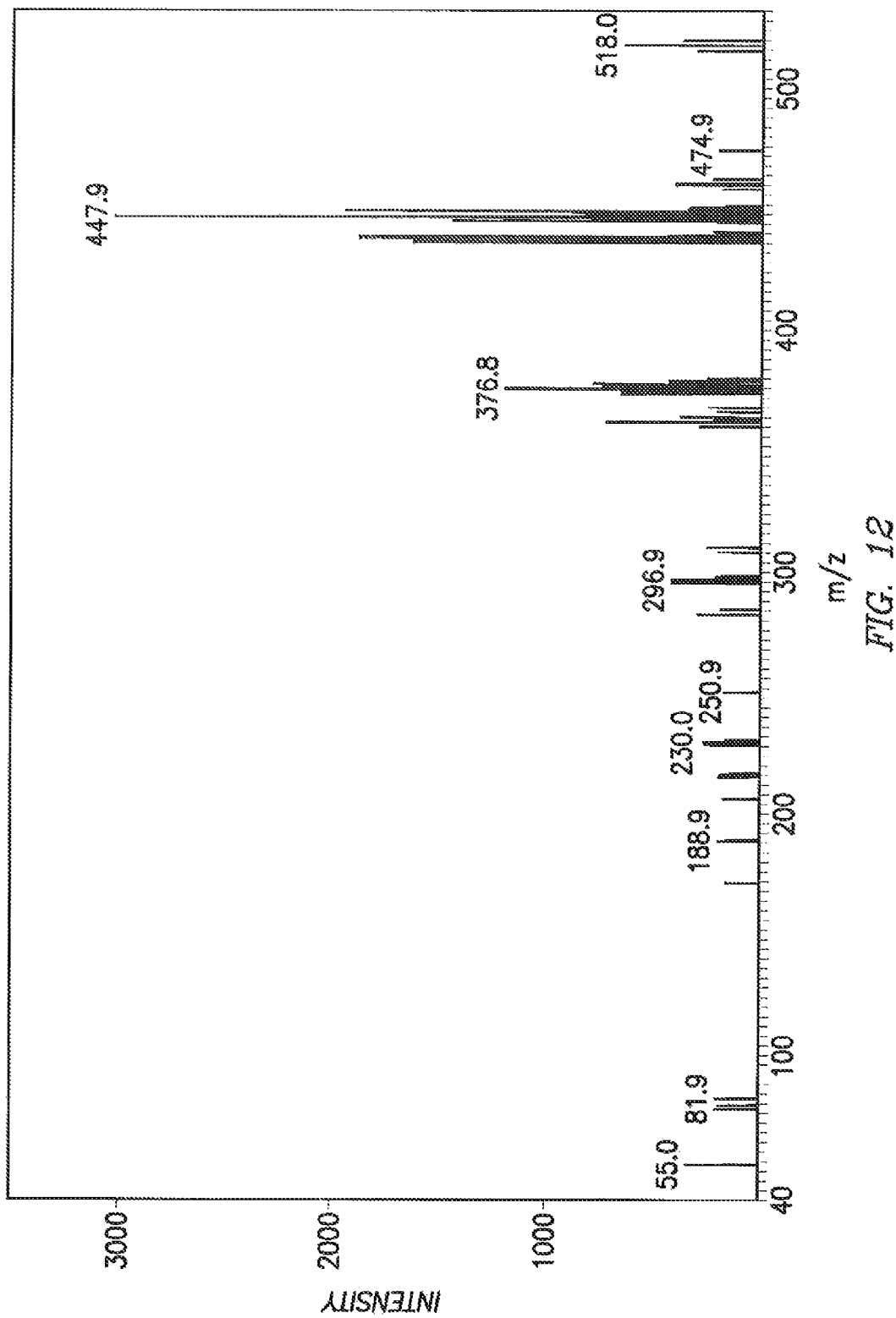
FIG. 12 depicts a mass spectroscopy spectrum of 2,6-dibromo-4,8-dihexylbenzo[1,2-d:4,5-d']bis(thiazole).

FIG. 12 depicts a mass spectroscopy spectrum of 2,6-dibromo-4,8-dihexylbenzo[1,2-d:4,5-d']bis(thiazole).

Figure 13:
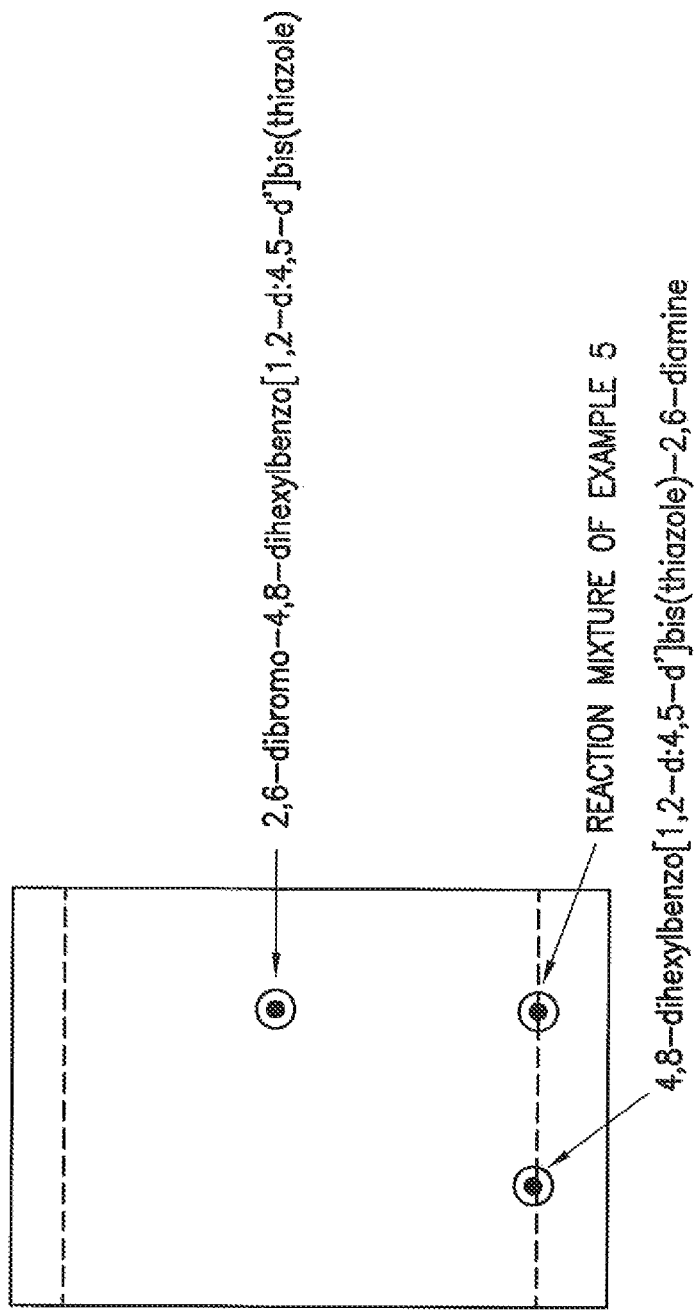
FIG. 13 depicts the results of a thin layer chromatography of 2,6-dibromo-4,8-dihexylbenzo[1,2-d:4,5-d']bis(thiazole), 4,8-dihexylbenzo[1,2-d:4,5-d']bis(thiazole)-2,6-diamine and the reaction mixture of Example 5.

FIG. 13 depicts the results of a thin layer chromatography of 2,6-dibromo-4,8-dihexylbenzo[1,2-d:4,5-d']bis(thiazole), 4,8-dihexylbenzo[1,2-d:4,5-d']bis(thiazole)-2,6-diamine and the reaction mixture of Example 5.

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A process comprising the step of:
   (a) synthesizing 2,6-dibromo-4,8-dihexylbenzo[1,2-d:4,5-d']bis(thiazole) from 2,5-dihexylbenzene-1,4-diamine.

2. The process of claim 1, wherein 2,5-dihexylbenzene-1,4-diamine is synthesized from 1,4-dibromohexyl benzene prior to synthesizing 2,6-dibromo-4,8-dihexylbenzo[1,2-d:4,5-d']bis(thiazole).

3. The process of claim 2, wherein 1,1'-(2,5-dihexyl-1,4-phenylene)bis(thiourea) is synthesized from 2,5-dihexylbenzene-1,4-diamine prior to synthesizing 2,6-dibromo-4,8-dihexylbenzo[1,2-d:4,5-d']bis(thiazole).

4. The process of claim 3, wherein 4,8-dihexylbenzo[1,2-d:4,5-d']bis(thiazole)-2,6-diamine is synthesized from 1,1'-(2,5-dihexyl-1,4-phenylene)bis(thiourea) prior to synthesizing 2,6-dibromo-4,8-dihexylbenzo[1,2-d:4,5-d']bis(thiazole).

5. The process of claim 2, wherein N,N'-(((2,5-dihexyl-1,4-phenylene)bis(azanediyl))bis(carbonothioyl))dibenzamide is synthesized from 2,5-dihexylbenzene-1,4-diamine prior to synthesizing 2,6-dibromo-4,8-dihexylbenzo[1,2-d:4,5-d']bis(thiazole).

6. The process of claim 5, wherein 1,1'-(2,5-dihexyl-1,4-phenylene)bis(thiourea) is synthesized from N,N'-(((2,5-dihexyl-1,4-phenylene)bis(azanediyl))bis(carbonothioyl))dibenzamide prior to synthesizing 2,6-dibromo-4,8-dihexylbenzo[1,2-d:4,5-d']bis(thiazole).

7. The process of claim 1, wherein the 2,6-dibromo-4,8-dihexylbenzo[1,2-d:4,5-d']bis(thiazole) is used in the synthesis of push-pull conjugated copolymers as donors of organic cells.

8. A process comprising the steps of:
   (a) synthesizing 2,5-dihexylbenzene-1,4-diamine from 1,4-dibromohexyl benzene;
   (b) synthesizing 1,1'-(2,5-dihexyl-1,4-phenylene)bis(thiourea) from 2,5-dihyxylbenzene-1,4-diamine;
   (c) synthesizing 4,8-dihexylbenzo[1,2-d:4,5-d']bis(thiazole)-2,6-diamine from 1,1'-(2,5-dihexyl-1,4-phenylene)bis(thiourea); and
   (d) synthesizing 2,6-dibromo-4,8-dihexylbenzo[1,2-d:4,5-d']bis(thiazole) from 4,8-dihexylbenzo[1,2-d:4,5-d']bis(thiazole)-2,6-diamine.

9. A process comprising the steps of:
   (a) synthesizing 2,5-dihexylbenzene-1,4-diamine from 1,4-dibromohexyl benzene;
   (b) synthesizing N,N'-(((2,5-dihexyl-1,4-phenylene)bis(azanediyl))bis(carbonothioyl))dibenzamide from 2,5-dihyxylbenzene-1,4-diamine;
   (c) synthesizing 1,1'-(2,5-dihexyl-1,4-phenylene)bis(thiourea) from N,N'-(((2,5-dihexyl-1,4-phenylene)bis(azanediyl))bis(carbonothioyl))dibenzamide;
   (d) synthesizing 4,8-dihexylbenzo[1,2-d:4,5-d']bis(thiazole)-2,6-diamine from 1,1'-(2,5-dihexyl-1,4-phenylene)bis(thiourea); and
   (e) synthesizing 2,6-dibromo-4,8-dihexylbenzo[1,2-d:4,5-d']bis(thiazole) from 4,8-dihexylbenzo[1,2-d:4,5-d']bis(thiazole)-2,6-diamine.

* * * * *